United States Patent [19]

Dorhofer et al.

[11] 4,045,570
[45] Aug. 30, 1977

[54] HETEROCYCLIC S-IMINO-S-OXIDES

[75] Inventors: Günther Dörhöfer, Allschwil; Roland Heckendorn, Arlesheim; Erich Schmid, Basel; Angelo Storni, Rheinfelden; Armin Züst, Birsfelden, all of Switzerland

[73] Assignee: Ciba-Geigy Corporation, Ardsley, N.Y.

[21] Appl. No.: 575,319

[22] Filed: May 7, 1975

[30] Foreign Application Priority Data

May 10, 1974 Switzerland .................. 6423/74

[51] Int. Cl.² ........................................ C07D 337/14
[52] U.S. Cl. .............................. 424/275; 260/327 B; 260/329 HS; 260/332.3 P; 260/332.5
[58] Field of Search ...... 260/327 B, 329 HS, 332.3 P, 260/332.5; 424/275

[56] References Cited

U.S. PATENT DOCUMENTS

| | | | |
|---|---|---|---|
| 3,356,680 | 12/1967 | Schindler et al. | 260/268 |
| 3,379,729 | 4/1968 | Protiva et al. | 260/268 |
| 3,600,392 | 8/1971 | Zust et al. | 260/268 |
| 3,636,045 | 1/1972 | Blattner et al. | 260/326.5 |
| 3,682,959 | 8/1972 | Blattner et al. | 260/326.9 |
| 3,755,357 | 8/1973 | Schindler et al. | 260/326.9 |
| 3,978,052 | 8/1976 | Stoss et al. | 260/243 A |

FOREIGN PATENT DOCUMENTS

| | | | |
|---|---|---|---|
| 2,240,921 | 3/1975 | France | 260/327 |
| 2,341,653 | 2/1975 | Germany | 260/327 |

*Primary Examiner*—Cecilia M. S. Jaisle
*Attorney, Agent, or Firm*—Joseph G. Kolodny; John J. Maitner; Theodore O. Groeger

[57] ABSTRACT

The invention relates to new heterocyclic S-imino-S-oxides of the formula I

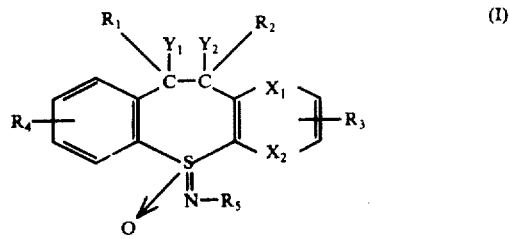

in which one of the symbols $X_1$ and $X_2$ denotes a direct bond and the other denotes the vinylene group —CH=CH— or the epithio radical —S—, $Y_1$ and $Y_2$ conjointly denote an additional bond or one of the symbols denotes hydrogen and the other denotes hydrogen or, conjointly with the symbol $R_1$ or $R_2$, which is present on the same carbon atom, denotes the oxo radical, one of the symbols $R_1$ and $R_2$ denotes hydrogen or lower alkyl and the other denotes hydrogen or lower alkyl or, conjointly with the symbol $Y_1$ or $Y_2$, which is present on the same carbon atom, denotes the oxo radical, or, if $Y_1$ and $Y_2$ conjointly denote an additional bond, also denotes lower alkoxy, and $R_3$ and $R_4$ independently of one another denote hydrogen, halogen up to atomic number 35, lower alkyl, lower alkoxy or trifluoromethyl and $R_5$ denotes hydrogen or lower alkyl, and to their acid addition salts in particular the pharmaceutically with inorganic and organic acceptable acid addition salts. These new compounds possess valuable pharmacological properties. In particular they have an anticonvulsive activity and are useful for the treatment of epilepsy and of states of tension and states of agitation.

14 Claims, No Drawings

HETEROCYCLIC S-IMINO-S-OXIDES

DETAILED DESCRIPTION

The present invention relates to new heterocyclic S-imino-S-oxides and their acid addition salts to therapeutic preparations which contain these new substances, and their use.

The compounds according to the invention correspond to the general formula I

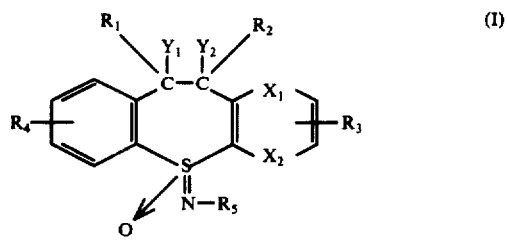

in which one of the symbols $X_1$ and $X_2$ denotes a direct bond and the other denotes the vinylene group —CH=CH— or the epithio radical —S—, $Y_1$ and $Y_2$ conjointly denote an additional bond or one of the symbols denotes hydrogen and the other denotes hydrogen or, conjointly with the symbol $R_1$ or $R_2$ which is present on the same carbon atom, denotes the oxo radical, one of the symbols $R_1$ and $R_2$ denotes hydrogen or lower alkyl and the other denotes hydrogen or lower alkyl or, conjointly with the symbol $Y_1$ or $Y_2$, which is present on the same carbon atom, denotes the oxo radical, or, if $Y_1$ and $Y_2$ conjointly denote an additional bond, also denotes lower alkoxy, and $R_3$ and $R_4$ independently of one another denote hydrogen, halogen up to atomic number 35, lower alkyl, lower alkoxy or trifluoromethyl and $R_5$ denotes hydrogen or lower alkyl.

In the preceding and the following text lower groups are understood to be those with at most 7, and preferably at most 4, carbon atoms. $R_1$ and $R_2$ as lower alkyl are above all methyl and as lower alkoxy are above all methoxy but can also be, for example, ethyl, propyl, butyl or isobutyl or ethoxy, propoxy, isopropoxy, butoxy or isobutoxy. $R_3$ and $R_4$, independently of one another, as halogen are, for example, bromine and preferably fluorine or chlorine, as lower alkyl are, for example, ethyl, propyl, isopropyl, butyl, sec.-butyl, tert.-butyl, and also pentyl, 1,1-dimethylpropyl, hexyl, 1-methylpentyl, heptyl or 1-methylhexyl, but above all methyl; and as lower alkoxy are, for example, ethoxy, propoxy, isopropoxy, butoxy, isobutoxy, and also pentyloxy, isopentyloxy, 2,2-dimethylpropoxy, hexyloxy or heptyloxy, but above all methoxy. If $X_1$ or $X_2$ denotes the epithio radical, preferably at least one of the symbols $R_3$ and $R_4$, especially $R_3$, represents hydrogen.

The compounds of the general formula I and the acid addition salts of these compounds possess valuable pharmacological properties. In particular they have an anticonvulsive action and they also have a moderately depressant action on the central nervous system. The anticonvulsive activity can be demonstrated in animal experiments, for example in the electric shock test on rats when doses of 10-60 mg/kg are administered perorally and on mice when doses of 20-70 mg/kg are administered perorally, and also in the pentetrazol cramp test and the strychnine cramp test. At the same time the toleration and therapeutic index are favourable. These properties characterise the compounds of the general formula I and their pharmaceutically acceptable salts with inorganic and organic acids as anticonvulsants, which can be used especially for treatment of epilepsy and of tension and states of agitation.

The invention relates especially to compounds of the general formula I, in which $Y_1$ and $Y_2$ denote hydrogen or conjointly denote an additional bond, $R_1$ and $R_2$ denote hydrogen or methyl, $R_3$ and $R_4$ independently of one another denote hydrogen, halogen up to atomic number 35, methyl, methoxy or trifluoromethyl and $R_5$ denotes hydrogen or methyl, whilst $X_1$ and $X_2$ have the meaning indicated under the formula I, and their addition salts, especially the pharmaceutically acceptable addition salts with inorganic and organic acids. The invention particularly relates to compounds of the general formula I, in which $X_1$ denotes a direct bond and $X_2$ denotes the vinylene group or the epithio radical, $Y_1$ and $Y_2$ denote hydrogen or conjointly denote an additional bond, $R_1$, $R_2$ and $R_3$ denote hydrogen, $R_4$ denotes hydrogen, halogen up to atomic number 35 or methoxy, and $R_5$ denotes hydrogen or methyl, and their addition salts, especially the pharmaceutically acceptable addition salts with inorganic and organic acids. The invention relates above all to compounds of the general formula I, in which $X_1$, $X_2$, $Y_1$, $Y_2$, $R_1$, $R_2$ and $R_3$ have the meaning indicated immediately above, $R_4$ denotes hydrogen or, if $X_2$ is a vinylene radical, can also denote chlorine or methoxy in the 2- or 8-position and $R_5$ denotes methyl, or above all, hydrogen, such as 5,5-dihydro-5-imino-dibenzo[b,f]thiepine-5-oxide, and the pharmaceutically acceptable acid addition salts of these compounds with inorganic and organic acids.

The new heterocyclic S-imino-S-oxides of the general formula I and their acid addition salts are manufactured according to the invention by a. mono-oxidising a compound of the general formula II

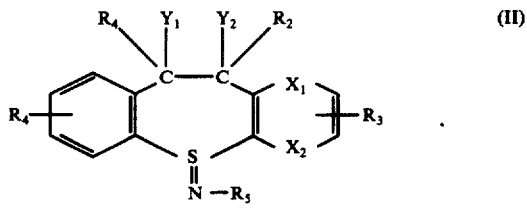

in which $X_1$, $X_2$, $Y_1$, $Y_2$, $R_1$, $R_2$, $R_3$, $R_4$ and $R_5$ have the meaning indicated under the formula I, or b. reacting a compound of the general formula III

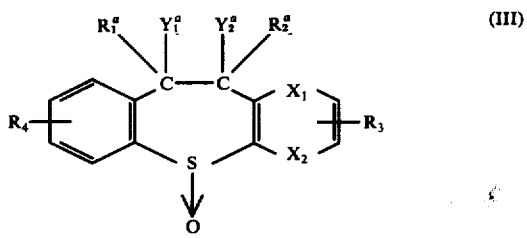

in which $Y_1{}^1$ and $Y_2{}^a$ each denote hydrogen or conjointly denote an additional bond and $R_1{}^1$ and $R_2{}^a$ independently of one another denote hydrogen or lower alkyl and $X_1$, $X_2$, $R_3$ and $R_4$ have the meaning indicated under the formula I, with a hydroxylamine derivative of the general formula IV

 (IV)

in which $R_6$ denotes a hydroxyl group or a hydrocarbon radical which optionally carries one or more inert substituents, and $R_5$ has the meaning indicated under the formula I, or with hydrazoic acid, or c. treating a compound of the general formula V

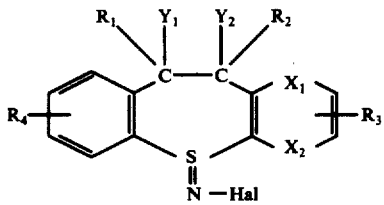 (V)

in which Hal denotes halogen, especially chlorine or bromine, and $X_1$, $X_2$, $Y_1$, $Y_2$, $R_1$, $R_2$, $R_3$ and $R_4$ have the meaning indicated under the formula I, with a base, or d. hydrolysing a compound of the general formula VI

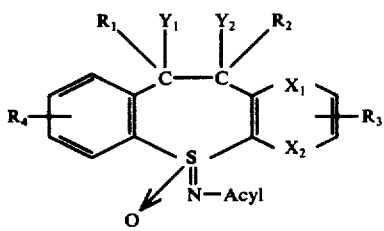 (VI)

in which Acyl denotes the acyl radical of an organic sulphonic acid or of a strong carboxylic acid, and $X_1$, $X_2$, $Y_1$, $Y_2$, $R_1$, $R_2$, $R_3$ and $R_4$ have the meaning indicated under the formula I, and optionally liberating a compound of the general formula I from an initially obtained acid addition salt of the latter and/or converting a compound of the general formula I, obtained in accordance with one of the abovementioned processes, into an addition salt with an inorganic or organic acid.

The mono-oxidation of a compound of the general formula II can be carried out by means of diverse types of oxidising agent, preferably in an acid medium and above all in a neutral medium. Examples of oxidising agents which can be used are periodic acid or, when the starting material of the general formula II is employed as an addition salt with a strong acid, especially as the hydrochloride, more advantageously in practice an alkali metal periodate, such as, for example, sodium meta-periodate or potassium metaperiodate. Under the reaction conditions these oxidising agents supply one equivalent of oxygen and are therefore preferably employed in an approximately equimolar to about 1.5-fold molar amount. The oxidation is carried out, for example, in water or in a mixture of water and a lower alkanol, such as, for example, methanol, ethanol, isopropanol or butanol, at temperatures between about 0° and 100° C or the boiling point of the reaction medium, if this is lower, and preferably between room temperature and about 65° C. Since the starting material of the formula II is a stronger base than the end substance of the general formula I, the course of the reaction can easily be monitored with the aid of the change in the pH of the reaction mixture.

Examples of further oxidising agents, and appropriate solvents or diluents, which can be used are potassium permanganate, for example in absolute acetonitrile, peroxy compounds, such as hydrogen peroxide, for example in acetic acid, organic peroxy acids, such as peroxyacetic acid in acetic acid or peroxybenzoic acid and also m-chloroperoxybenzoic acid in halogenated hydrocarbons, such as methylene chloride or chloroform, inorganic peroxy acids and their salts, such as, for example, potassium peroxysulphate in acetic acid, or higher metal oxides, such as chromium trioxide, for example in aqueous acetone or in acetic acid. Of these, oxidising agents which can be employed in the absence of water and of acid are particularly advantageous for the oxidation of compounds of the general formula II in which $R_1$ or $R_2$ denotes lower alkoxy, $R_2$ or $R_1$ denotes hydrogen or lower alkyl and $Y_1$ and $Y_2$ conjointly denote an additional bond.

The manufacture of the starting materials of the general formula II, which are themselves new, is explained further below.

The reaction of compounds of the general formula III with hydroxylamine derivatives of the general formula IV in accordance with (b) is carried out in a manner which is in itself known, for example at temperatures between 0° C and 60° C, especially at room temperature, in an organic solvent, such as, for example, methylene chloride, chloroform or methanol. A suitable hydroxylamine derivative of the general formula IV is, for example, an O-arenesulphonylhydroxylamine, such as O-mesitylenesulphonyl-hydroxylamine. The desired compound of the general formula I can be liberated from its sulphonic acid salt or sulphuric acid salt, which is initially obtained, in a customary manner, that is to say by adding a basic substance or the aqueous solution of such a substance, such as, for example, aqueous sodium bicarbonate, sodium carbonate or sodium hydroxide solution.

The reaction of compounds of the general formula III with hydrazoic acid is carried out, for example, in an inert organic solvent, especially a halogenated hydrocarbon, such as, for example, chloroform, at temperatures between room temperature and about 50° C, taking the care demanded for reactions with hydrazoic acid. The hydrazoic acid employed is preferably gradually liberated in situ from one of its salts, for example the sodium salt, by the dropwise addition of a mineral acid, such as, for example, concentrated sulphuric acid, or a Lewis acid. The manufacture of the starting materials of the general formula III will be explained in more detail below.

A suitable base for treatment of a starting material of the general formula V in accordance with process (c) is, for example, an alkali metal hydroxide, such as sodium hydroxide, for example in a lower alkanol, such as methanol. The reaction is carried out, for example, at room temperature up to about 70° C. The N-halogeno-S-imino compounds of the general formula V, which are required as starting materials, are preferably manufactured immediately before the treatment with bases from the S-imino compounds of the general formula II, the manufacture of which is explained below, by reaction with reactive N-halogeno-imides, -sulphonamides or -carboxamides or with corresponding heterocyclic N-halogenated compounds, for example with N-chlorosuccinimide or N-bromosuccinimide, in a solvent which is inert under the reaction conditions, that is to say at room temperature, such as, for example, acetone, separated off under gentle conditions and further processed without further purification.

In the starting materials of the general formula VI for the hydrolysis in accordance with (d), acyl, as the acyl radical of an organic sulphonic acid, is, for example, the acyl radical of methanesulphonic acid, benzenesulphonic acid, o- or p-toluenesulphonic acid, o- or p-chlorobenzenesulphonic acid or m-nitrobenzenesulphonic acid, and, as the acyl radical of a strong carboxylic acid, is, for example, the acyl radical of a lower halogenated alkanoic acid, such as trichloroacetic acid, dichloroacetic acid or trifluoroacetic acid, or the acyl radical of a nitrated benzoic acid, such as o- or p-nitrobenzoic acid. Preferably, acyl is an acyl radical which ensures ready accessibility of the corresponding compound of the general formula VI. For this reason, in accordance with the manufacturing processes, which are explained further below, for starting materials of the general formula VI, the p-tolysulphonyl radical on the one hand and the o- or p-nitrobenzoyl radical on the other hand are to be singled out in particular. The hydrolysis can be carried out in an acid or an alkaline medium, for example with strong acids, such as concentrated sulphuric acid, at room temperature or with dilute sulphuric acid or concentrated or dilute hydrochloric acid at room temperature up to about 100° C, or with aqueous or preferably aqueous-lower alkanolic alkali metal hydroxide solutions, such as, for example, aqueous-methanolic sodium hydroxide or potassium hydroxide solution, at room temperature up to about 100° C or the boiling point of the reaction medium if this is lower.

The compounds of the general formula I, according to the invention, can, in turn, be converted by various processes into other compounds which fall under this general formula. For example, e. compounds of the general formula I, in which $Y_1$ and $Y_2$ denote hydrogen and $R_1$ and $R_2$ denote hydrogen or lower alkyl, whilst $X_1$, $X_2$, $R_3$, $R_4$ and $R_5$ have the meaning indicated under the formula I, are obtained by hydrogenating a compound of the general formula Ia,

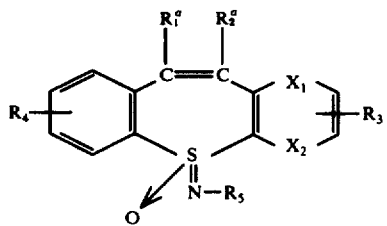

in which $R_1^a$ and $R_2^a$ independently of one another denote hydrogen or lower alkyl and $X_1$, $X_2$, $R_3$, $R_4$ and $R_5$ have the meaning indicated under the formula I, or f. compounds of the general formula I, in which $R_5$ denotes lower alkyl and $Y_1$, $Y_2$, $R_1$ and $R_2$ have the meaning indicated under the formula I, with the exception of an oxo radical formed by $Y_1$ and $R_1$ or $Y_2$ and $R_2$, whilst $X_1$, $X_2$, $R_3$ and $R_4$ have the meaning indicated under the formula I, are obtained by reacting a compound of the general formula Ib,

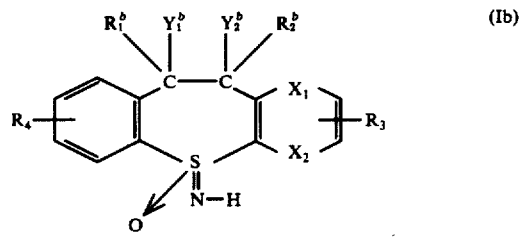

in which $Y_1^b$ and $Y_2^b$ each denote hydrogen or conjointly denote an additional bond and $R_1^b$ and $R_2^b$ independently of one another denote hydrogen or lower alkyl and one of these symbols can also denote lower alkoxy, and $X_1$, $X_2$, $R_3$ and $R_4$ have the meaning indicated under the formula I, with a lower oxoalkane under reducing conditions or, either in the presence of an acid-binder or after conversion into a N-alkali metal derivative, with a reactive ester of a lower alkanol, or g. compounds of the general formula I, in which $R_1$ conjointly with $Y_1$, or $R_2$ conjointly with $Y_2$, denotes an oxo radical and $R_2$ and $Y_2$ or $R_1$ and $Y_1$ each denote hydrogen, whilst $X_1$, $X_2$, $R_3$, $R_4$ and $R_5$ have the meaning indicated under the formula I, are obtained by hydrolysing a compound of the general formula Ic,

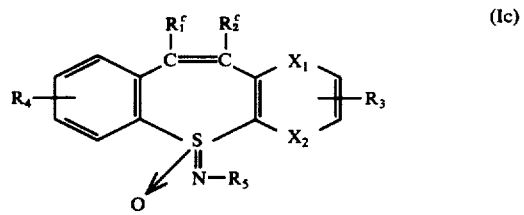

in which one of the symbols $R_1^c$ and $R_2^c$ denotes lower alkoxy and the other denotes hydrogen or lower alkyl, and $X_1$, $X_2$, $R_3$, $R_4$ and $R_5$ have the meaning indicated under the formula I, in an alkaline medium or preferably an acid medium.

The hydrogenation of the compounds of the general formula Ia in accordance with (e) is carried out, for example, in the presence of tris-triphenylphosphine-rhodium chloride in an inert organic solvent, such as, for example, benzene, at hydrogen pressures of about 20-100 bars, preferably 50-60 bars, and temperaures between 50° and 120° C in a closed vessel.

To carry out the first alkylation process, mentioned under (g), for example, an oxoalkane with 1-4 carbon atoms, especially formaldehyde, is reacted with a compound of the general formula Ib and the reaction product is reduced in situ, formic acid at or slightly below the boiling point of the reaction mixture preferably being employed as the reagent. Reactive esters of lower alkanols which are suitable for reaction with compounds of the general formula Ib, or the alkali metal drivatives thereof, are, for example, esters with strong acids, such as the halides, sulphates and organic sulphonic acid esters, for example lower alkanesulphonic acid esters and arenesulphonic acid esters. Methyl iodide, ethyl iodide, ethyl bromide, propyl bromide, butyl bromide and isobutyl bromide, dimethyl sulphate, diethyl sulphate, methanesulphonic acid methyl ester and p-toluenesulphonic acid methyl ester may be mentioned merely as representatives of these types of compound. Acid-binders which can be used are inorganic and organic basic substances, such as, for example, sodium, carbonate, potassium carbonate, triethylamine or N-ethyl-N,N-diisopropylamine. The reactions are carried out, for example, in N,N,N',N'N",N"-hexamethylphosphoric acid triamide, dimethylsulphoxide or dimethylformamide at 0° C to about 100° C. The alkali metal compounds, especially sodium or lithium compounds of compounds of the general formula Ib, which are used, if desired, as direct starting materials, are preferably manufactured in the same solvent, immediately prior to the further reaction, by the action of an alkali metal compound, such as sodium hydride, sodium amide or lithium amide, on the corresponding compound of the general formula Ib.

The hydrolysis of compounds of the general formula Ic in accordance with (g) is carried out, for example, in dilute aqueous or lower alkanolic-aqueous mineral acids, especially hydrochloric acid, at room temperature up to about 100° C or the boiling point of the reaction medium, if this is lower. The hydrolysis can also be carried out in the same operation as the hydrolytic removal, mentioned under (d), or an acyl group from a compound of the general formula VI, in which $Y_1$ and $Y_2$ conjointly denote an additional bond and $R_1$ and $R_2$ correspond to the definition indicated for $R_1{}^c$ and $R_2{}^c$ under the formula Ic.

The starting substances of the general formulae II, III, V and VI for the processes mentioned under (a) to (e) are themselves new substances, all of which can be manufactured starting from compounds of the general formula VII

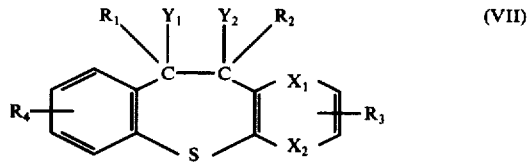
(VII)

in which $X_1$, $X_2$, $Y_1$, $Y_2$, $R_1$, $R_2$, $R_3$ and $R_4$ have the meaning indicated under the formula I. Of the compounds of the general formula VII, individual representatives in which $R_1$ and $R_2$ denote hydrogen or lower alkyl and $Y_1$ and $Y_2$ denote hydrogen or conjointly denote an additional bond, are known, such as dibenzo[b,f]thiepine and 10,11-dihydro-dibenzo[b,f] thiepine [compare J.O. Jilek et al, Monatsh. Chem. 96, 182–207 (1965)], 2-fluoro- and 2-bromo-dibenzo[b,f] thiepine [compare J.O. Jilek et al., Collect. Czech. Chem. Commun. 33, 1831–45 (1968)], 2-methoxy-dibenzo[b,f]thiepine, [K. Pelz et al., Collect, Czech. Chem. Commun. 33, 1895-1910]. 2-(trifluoromethyl)-dibenzo[b,f]thiepine, [compare L. Pelz et al., Collect. Czech. Chem. Commun. 34, 3936-43 (1969)],10-methyl -,2-chloro-10-methyl-, 8-chloro-10-methyl-, 2-methoxy10-methyl- and 8-methoxy-10-methyl-dibenzo[b,f]thiepine, [compare U.S. Pat. No. 3,356,680], 10,11-dimethyldibenzo[b,f]thiepine, [compare M.M. Urberg and E.T. Kaiser, J. Amer. Chem. Soc. 89, 5931, (1967)], 2-chloro-10,11-dimethyl-, 2-methoxy-10,11-dimethyl- and 2,10,11-trimethyl-dibenzo[b,f,] thiepine, (compare U.S. Pat. No. 3,636,045), 2-(trifluoromethyl)-10,11-dimethyl-dibenzo[b,f]thiepine, (compare U.S. Pat. No. 3,755,357), thieno[2,3-b][1]benzothiepine [compare M. Rajsner et al., Il Farmaco, Ed. Sci. 23, 140 (1968)] and 2-chloro-thieno[2,3-b][1]benzothiepine [compare M. Rajsner et al., Collect. Czech. Chem. Commun. 35, 378-382 (1970)] as well as 4,5-dimethylthieno[2,3-b][1]benzothiepine and 9,10-dimethylthieno[3,2][1]benzothiepine [compare U.S. Pat. No. 3,682,959].

Further compounds of the general formula VII wherein $Y_1$, $Y_2$, $R_1$ and $R_2$ have the meanings already mentioned can be manufactured analogously to the known compounds, the 1-methylpiperazine in the process of J.O. Jilek et al., and K. Pelz et al. being replaced by a tertiary organic base, such as diisopropylethylamine, or an inorganic base as an agent for removing hydrogen halide, in order to obtain the compounds of the general formula VII as the sole reaction products.

Compounds of the general formula VII, in which $Y_1$ and $Y_2$ denote hydrogen, can also, in general, be manufactured by catalytic hydrogenation of corresponding compounds having an additional bond as $Y_1$ and $Y_2$, for example in the presence of tris-triphenylphosphine-rhodium chloride in benzene at moderately elevated temperatures and hydrogen pressures.

Some representatives of the compounds of the general formula VII, in which $R_1$ conjointly with $Y_1$ or $R_2$ conjointly with $Y_2$ denotes an oxo radical, are also known, for example dibenzo[b,f]thiepin-10(11H)-one [compare J.O. Jilek et al., Monatsh. Chem. 96, 182–207 (1965)], 2-chloro-, 3-chloro-, 8-chloro-, 2-methoxy- and 8-methyl-dibenzo[b,f]thiepin-10(11H)-one and also 11-methyl, 11-ethyl-, 8,11-dimethyl, 2-chloro-11-methyl-, and 2-methoxy-11-methyl-dibenzp[b,f]thiepin-10(11H)-one [compare U.S. Pat. No. 3,356.680], 8-fluoro and 8-bromodibenzo[b,f]thiepin-10(11H-one [compare J.P. Jilek et al., Collect. Czech. Chem. Commun. 33, 1831–45 (1968), 8-(methylthio)- and 8-tert.-butyl-dibenzo[b,f]thiepin-10(11H)-one [compare K. Pelz et al., Collect, Czech. Chem. Commun. 33, 1895–1910], 2; -(trifluoromethyl)-, 7-(trifluoromethyl)- and 8-(trifluoromethyl)-dibenzo[b,f,]thiepin-10(11H)-one [compare K. Pelz et al., Collect. Czech. Chem. Commun. 34, 3930–43 (1969) and also U.S. Pat. No. 3,379,729], thieno[2,3-b][1]benzothiepin-4(5)-one [compare M. Rajsner et al., Il Farmaco, Ed. Sci. 23, 140 (1968)]. 2-chloroethieno [2,3-b][1 ]benzothiepin-4(5H)-one [compare M. Rajsner et al., Collect. Czech. Chem. Commun, 35, 378–82 (1970)] and thieno [3,2-b][1]benzothiepin-10(9H)-one [compare U.S. Pat. No. 3,600,392]. Further compounds of the general formula VII with a substituent of this type on the seven-membered ring can be manufactured analogously to the known compounds.

Compounds of the general formula VII, in which $R_1$ or $R_2$ is lower alkoxy and $Y_1$ and $Y_2$ conjointly denote an additional bond, can be manufactured, for example, from the corresponding compounds, in which $R_1$ and $R_2$ denotes hydrogen and $Y_1$ and $Y_2$ conjointly denote an additional bond, by addition of bromine to the bridge member and reaction of the resulting dibromo compound with the twice molar amount of a lower alkali metal alkoxide, for example sodium methoxide or sodium ethoxide, in the corresponding lower alkanol. Furthermore, compounds of the general formula VII with substitutents of this type on the seven-membered ring can also be obtained, in some cases together with a certain proportion of the corresponding C-alkylation product, by reacting the alkali metal derivatives of corresponding compounds of the general formula VII, in which $R_1$ or $R_2$ together with the symbol $Y_1$ or $Y_2$, which is present on the same carbon atom, denotes the oxo radial, with a lower alkyl halide in the corresponding lower alkanol or a suitable inert organic solvent, such as N,N,N'N',N",N"-hexamethylphosphoric acid triamide, dimethylsulphoxide or dimethylformamide.

The direct starting materials of the general formula II for the process a) are manufactured from the compounds of the general formula VII by reacting the latter with a hydroxylamine derivative of the general formula IV, in which $R_6$ and $R_7$ have the meaning defined under this formula, and liberating the compound II, with the aid of a strong base, from the salt, which has initially formed, of the compound of the general formula II with the sulphonic acid which corresponds to the radial $R_7$ or with sulphuric acid. Thus, for example, analogously to a process described by Y. Tamura et al., Tetrahedron Letters 1972, 4137-4140, for the manufacture of N,N-diphenylsulphilimine, compounds of the general formula II can be reacted with O-meistylene-sulphonyl-hydroxylamine in methanol or methylene chloride at room temperature or moderately elevated temperature and the compounds of the general formula II can then be liberated by treating the resulting meistylenesulphonic acid salt with a methanolic sodium methoxide solution.

A further process for the manufacture of the starting materials of the general formula II consists in hydrolysing a compound of the general formula VIII

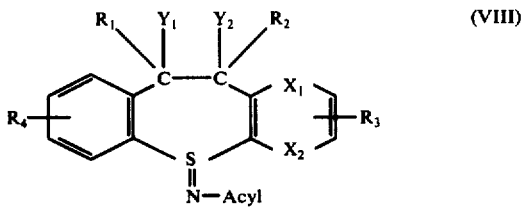

in which $X_1$, $X_2$, $Y_1$, $Y_2$, $R_3$ and $R_4$ have the meaning indicated under formula I and acyl has the meaning indicated under formula VI, analogously to process (e) for the manufacture of the compounds of the general formula I. Compounds of the general formula VIII, in which acyl in particular denotes the acyl radical of an organic sulphonic acid, such as, for example, the p-tolylsulphonyl radical, but, for example, can also denote the acyl radical of a lower halogenated alkanoic acid, such as, for example, the dichloroacetyl radical, can, in turn, be manufactured, for example, by reacting compounds of the general formula VII with the sodium compound of a corresponding N-chloroamide, for example the sodium compound of N-chloro-p-toluenesulphonamide, which is known as Chloramin T, analogously to a reaction which was first described by F. G. Mann and Wm. J. Pope, J. Chem. Soc. 121, 1052-5 (1922).

Finally, compounds of the general formula VII, especially those in which $Y_1$ and $Y_2$ denote hydrogen, can also be converted, analogously to a process described by B. Appel and W. Büchner, Chem. Ber. 95, 2220-2224 (1962), for the manufacture of S,S-bis-(p-methoxyphenyl)-sulphilimine, by the action of chlorine, for example as dry chlorine gas in a benzene solution, into the corresponding S,S-dichloro-S,S-dihydro compounds, such as, for example, 5,5-dichloro-5,5,10,11-tetrahydro-dibenzo[b,f]thiepines, which may be substituted in accordance with the definition of $R_1$, $R_2$, $R_4$ and $R_5$, and the latter compounds can be reacted with liquid ammonia or with anhydrous lower alkylamines to give iminium chlorides, which correspond to the desired starting materials of the general formula II. The compounds of the general formula II can be liberated from the iminium chlorides, for example by the action of sodium amide or a solution of sodium in liquid ammonia.

If desired, the compounds of the general formula II can be converted in a customary manner into their addition salts with inorganic and organic acids, such as, for example, the hydrochlorides.

Starting materials of the general formula III for process (b) can be manufactured by mono-oxidation of the corresponding compounds of the general formula VII, for example by means of hydrogen peroxide in an aqueous-lower alkanolic, especially aqueous-ethanolic, medium at a moderately elevated temperature up to the boiling point of the reaction medium, or by means of periodic acid, which is liberated in situ from sodium periodate, for example in an aqueous-methanolic medium at room temperature up to the boiling point of the reaction medium. Compounds of the general formula III, with the exception of the two representatives in which $R_1$ and $R_2$ both denote hydrogen or both denote methyl, $X_1$ denotes a vinylene group, $Y_1$ and $Y_2$ conjointly denote an additional bond an $R_3$ and $R_4$ denote hydrogen, have not been disclosed hitherto.

Starting materials of the general formula VI, in which acyl in particular denotes the acyl radical of an organic sulphonic acid, such as, for example, the p-tolylsulphonyl radical, or the acyl radical of a lower halogenated alkanoic acid, such as the dichloroacetyl radical, are obtained, for example, by oxidation of the corresponding compounds of the general formula VIII, which has been defined further above, analogously to the process mentioned under (a) for the manufacture of compounds of the general formula I. Starting materials of the general formula VI, which contain the p-or o-nitrobenzoyl radical as the acyl radical, are preferably manufactured analogously to a process described in German Offenlegungsschrift No. 2,220,256 by reacting compounds of the general formula III, which has been defined further above, with O-acetyl-p-nitrobenzhydroxamic acid or O-actyl-o-nitrobenzhydroxamic acid at elevated temperatures, preferably at 120°-150° C in the absence of solvents or diluents.

The present invention also relates to modifications of the processes mentioned under (a) to (g), and the preliminary stages thereof, in which a process is discontinued at any stage or in which a compound occurring at any stage as an intermediate product is used as a starting material and the missing steps are carried out or a starting material is formed under the reaction conditions or, optionally, is used in the form of a salt. Insofar as end products are obtained as racemates or racemate mixtures, these can, if desired, within the scope of the present invention, be separated and resolved into their antipodes.

The compounds of the general formula I obtained in accordance with the processes of the invention are converted, if desired, in a customary manner into their addition salts with inorganic and organic acids. For example, hydrochloric acid, hydrobromic acid, sulphuric acid, phosphoric acid, perchloric acid, methanesulphonic acid, ethanesulphonic acid, 2-hydroxyethanesulphonic acid, acetic acid, lactic acid, succinic acid, fumaric acid, maleic acid, malic acid, tartaric acid, citric acid, benzoic acid, salicyclic acid, phenylacetic acid, mandelic acid or embonic acid are used for salt formation, preferably in the presence of a solvent, such as, for example, acetone, methanol, ethanol, ether or mixtures thereof.

The compounds of the general formula I and their pharmaceutically acceptable acid addition salts are preferably administered perorally. The daily doses vary between 0.5 and 25 mg/kg for warm-blooded animals. Suitable dosage units, such as dragees or tablets, preferably contain 2.5 to 100 mg of an active substance according to the invention, that is to say a compound of the general formula I or a pharmaceutically acceptable acid addition salt of these substances. To manufacture these units, the active substance is combined with solid pulverulent excipients, such as lactose, saccharose, sorbitol and mannitol; starches, such as potato starch, maize starch or amylopectin, and also laminaria powder or citrus pulp powder; cellulose derivatives or gelatine, optionally with the addition of lubricants, such as magnesium stearate or calcium stearate or polyethylene glycols, to give tablets or dragee cores. The latter are coated, for example, with concentrated sugar solutions which, for example, can also contain gum arabic, talc and/or titanium dioxide, or with a lacquer dissolved in readily volatile organic solvents or solvent mixtures. Colorants can be added to these coatings, for example to characterise various doses of active substance. Other suitable oral dosage units are syrups or shakes and also push-fit capsules made of gelatine as well as soft, closed capsules made of gelatine and a plasticiser, such as glycerol. The former preferably contain the active substance as granules in a mixture with lubricants, such as talc or magnesium stearate, and optionally stabilisers, such as sodium metabisulphite or ascorbic acid.

The following instruction is intended to explain the manufacture of tablets in more detail: 250.0 g of 5,5-dihydro-5-imino-dibenzo[b,f]thiepine-5-oxide are mixed with 500 g of lactose and 292 g of potato starch and the mixture is moistened with an alcoholic solution of 8 g of gelatine and granulated through a sieve. After drying, 60 g of potato starch, 60 g of talc, 10 g of magnesium stearate and 20 g of highly disperse silicon dioxide are mixed in and the mixture is pressed to give 10,000 tablets each 120 mg in weight and each containing 25 mg of active substance, which can optionally be provided with dividing grooes for finer adjustment of the dose.

The examples which follow illustrate the manufacture of the new compounds of the general formula I, and of starting materials not hitherto known, in more detail, but are not intended to restrict the scope of the invention in any way.

EXAMPLE 1

A solution of 10.5 g (0.040 mol) of 5,5-dihydro-5-iminodibenzo[b,f]thiepine hydrochloride in 150 ml of water and 50 ml of methanol is heated to 50° C and a solution of 9.5 g (0.044 mol) of sodium meta-periodate in 60 ml of water is added in the course of 30 minutes whilst stirring. The reaction mixture is stirred for 20 hours at a temperature of 60° - 65° C. Thereafter it is concentrated to half its volume in a waterjet vacuum, the pH value is then brought to 8-9 by means of a potassium carbonate solution and the mixture is then extracted with three times 150 ml of methylene chloride. The combined methylene chloride solutions are washed with water until neutral, dried over sodium sulphate and evaporated in a waterjet vacuum. 5,5-Dihydro-5-imino-dibenzo[b,f] thiepine-5-oxide remains as a residue and, after a single recrystallisation from isopropanol, melts at 153°-156° C.

The 5,5-dihydro-5-imino-dibenzo[b,f]thiepine, which is required as the starting material, can be manufactured as follows:

a. 12 g (0.057 mol) of O-mesitylenesulphonyl-hydroxylamine are added, at room temperature and whilst stirring, to a solution of 10 g (0.0475 mol) of dibenzo[b,f]thiepine in 600 ml of methanol. (Compare Y. Tamura, K. Sumoto, J. Minamikawa and M. Ideda, Tetrahedron Letters 1972, 4133). The reaction solution is stirred overnight at room temperature, concentrated in a waterjet vacuum, taken up in 300 ml of methylene chloride and treated with a methanolic sodium methylate solution, which is prepared by dissolving 1.32 g (0.057 gram atom) of sodium in 25 ml of methanol. The solution is stirred for 10 minutes at room temperature and then washed in a separating funnel with three times 100 ml of water. It is then dried over sodium sulphate and evaporated in a waterjet vacuum, an oil, which crystallises on prolonged standing, remaining as a residue. 5,5-Dihydro-5-imino-dibenzo[b,f]thiepine of melting point 124° C is obtained by recrystallisation from methanol.

1.058 g (0.0047 mol) of the resulting base are dissolved in 10 ml of acetone and neutralised accurately with 5 N ethanolic hyrochloric acid. The hydrochloride is precipitated by adding ether and is recrystallised from ethanol; melting point 265° C (decomposition).

EXAMPLE 2

A solution of 3.34 g (0.0156 mol) of sodium metaperiodate in 30 ml of water is added dropwise at 30° C in the course of 10 minutes to a solution of 2.96 g (0.010 mol) of 2-chloro-5,5-dihydro-5-imino-dibenzo[b,f]thiepine hydrochloride in 75 ml of methanol and 40 ml of water. The reaction mixture is stirred for 4 days at 30° C and thereafter, after the addition of saturated sodium chloride solution, is extracted three times with ethyl acetate. The organic phase is washed three times with cold 1 N hydrochloric acid, once with cold 1 N potassium bicarbonate solution and twice with water, dried over sodium sulphate and evaporated in vacuo. The residue is recrystallised from benzene with the addition of a little hexane. After drying, the resulting 2-chloro-5,5-dihydro-5-imino-dibenzo[b,f]thiepine-5-oxide melts at 122°-124° C.

The starting material is manufactured as follows:

a. 25.8 g (0.12 mol) of O-(mesitylenesulphonyl)-hydroxylamine is added at room temperature and whilst stirring to a solution of 24.2 g (0.10 mol) of 2-chloro-dibenzo[b,f]thiepine [compare J. O. Jilek et al., Collect. Czech. Chem. Commun. 33, 1831-45 (1968)] [compare Example 1a)]. The reaction solution is stirred for about 15 hours at room temperature and concentrated in a waterjet vacuum. 600 ml of methylene chloride and then a sodium methoxide solution, which is prepared by dissolving 2.76 g (0.012 gram atom) of sodium in 50 ml of methanol, are added to the concentrate. The resulting solution is stirred for 10 minutes at room temperature and then washed with three times 250 ml of water. It is then dried with sodium sulphate and evaporated in a waterjet vacuum. The residue is crystallised from benzene/petroleum ether, 2-chloro-5,5-dihydro-5-imino-dibenzo[b,f]-thiepine, of melting point 116°-117° C, being obtained.

The resulting base is dissolved in ethanol, ethanolic hydrochloric acid is added until there is an acid reaction and the resulting hydrochloride is caused to crystallise by adding ethyl acetate. After recrystallisation from ethanol/ethyl acetate, the hydrochloride metls at 230°–232° C.

EXAMPLE 3

A solution of 2.34 g (0.011 mol) of sodium metaperiodate in 22 ml of water is added dropwise at 25° C in the course of 30 minutes to a solution of 2.64 g (0.010 mol) of 5,5,10,11-tetrahydro-5-imino-dibenzo[b,f]thiepine hydrochloride in 65 ml of methanol and 44 ml of water. The reaction mixture is stirred for 18 hours at room temperature and then extracted three times with ethyl acetate, saturated sodium chloride solution being added. The organic phase is washed twice with ice-cold 1 N hydrochloric acid, once with ice cold 1 N potassium bicarbonate solution and twice with water, dried over sodium sulphate and evaporated in vacuo. The residue is recrystallised from benzene/hexane. After drying, the resulting 5,5,10,11-tetrahydro-5-imino-dibenzo[b,f]thiepine-5-oxide melts at 115°–117° C.

a. To manufacture the starting material, 8.05 g (0.038 mol) of 10,11-dihydro-dibenzo[b,f]thiepine are reacted with 10.2 g (0.047 mol) of O-mesitylenesulphonyl-hydroxylamine, analogously to Example 1a), and 5,5,10,11-tetrahydro-5-iminodibenzo[b,f]thiepine of melting point 204°–107° C is obtained; the hydrochloride of melting point 255° C (decomposition) is obtained from this.

EXAMPLE 4

A solution of 3.34 g (0.0156 mol) of sodium periodate in 30 ml of water is added dropwise at 30° C in the course of 10 minutes to a solution of 2.68 g (0.010 mol) of 10,10-dihydro-10-imino-thieno[2,3-b][1]benzothiepine hydrochloride in 75 ml of methanol and 40 ml of water. The reaction mixture is stirred for 4 days at 30° C and, after the addition of saturated sodium chloride solution, is then extracted three times with ethyl acetate. The organic phase is washed three times with cold 1 N hydrochloric acid, once with cold 1 N potassium bicarbonate solution and twice with water, dried over sodium sulphate and evaporated in vacuo. The residue is recrystallised from benzene with the addition of a little hexane. After drying, the resulting 10,10-dihydro-10-imino-thieno[2,3-b][1] benzothiepine-10-oxide melts at 143°–145° C a. To manufacture the starting material 8.1 g (0.037 mol) of thieno[2,3-b][1]benzothiepine are reacted with 9.6 g (0.044 mol) of O-mesitylenesulphonyl-hydroxylamine, analogously to Example 1a), 10,10-dihydro-10-imino-thieno [2,3-b][1]benzothiepine being obtained as an oil and being converted into the hydrochloride of melting point 205° C (decomposition).

EXAMPLE 5

11.3 g (0.05 mol) of dibenzo[b,f]thiepine-5-oxide are dissolved in 250 ml of absolute methylene chloride and 16 g (0.075 mol) of O-(mesitylenesulphonyl)-hydroxylamine [compare Y. Tamura, J. Minamikawa, U. Sumoto, S. Fujii and M. Ikeda, J. Org. Chem. 38, 1239 (1973)] are added in portions at room temperature whilst stirring. The reaction solution is then left to stand at room temperature for 16 hours. The methylene chloride solution is then washed three times with saturated sodium bicarbonate solution and once with water, dried over sodium sulphate and evaporated in a waterjet vacuum. The resulting crude product consists of unchanged dibenzo[b,f]thiepine-5-oxide and 5,5-dihydro-5-imino-dibenzo[b,f]thiepine-5-oxide. The crude product is chromatographed on 220 g of silica gel using methylene chloride to separate the two components. The first three fractions, each of 250 ml, elute dibenzo[b,f]thiepine-5-oxide of melting point 126°–132° C. Elution with methylene chloride/methanol, 99:1, gives pure 5,5-dihydro5-iminodibenzo[b,f]thiepine-5-oxide of melting point 157°–159° C.

The starting material is manufactureed as follows:

a. 41.9 g (0.2 mol) of dibenzo[b,f]thiepine [compare J. O. Jilek et al., Monatsh. Chem. 96, 182–207, especially 203(1965)] are dissolved in 60 ml of absolute ethanol at the reflux temperature and 160 ml of 30% strength aqueous hydrogen peroxide solution is added dropwise in the course of 30 minutes whilst stirring vigorously. The reaction mixture is boiled under reflux for 12 hours and is then poured into 1,200 ml of ice water. The precipitated reaction product is filtered off, washed well with cold water and recrystallised from ethanol. The resulting 2-dibenzo[b,f]thiepine5-oxide melts at 130°–137° C.

EXAMPLE 6

Analogously to Example 5, starting from 4.3 g (0.016 mol) of 2-chloro-10,11-dihydro-dibenzo[b,f]thiepine5-oxide and 9 g (0.042 mol) of O-(mesitylenesulphonyl)-hydroxylamine, 2-chloro-5,5,10,11-tetrahydro-5-iminodibenzo[b,f]thiepine-5-oxide is obtained as a pale yellowish oil.

The starting material is manufactured as follows:

a. 122.4 g (0.5 mol) of 2-chloro-dibenzo[b,f]thiepine [compare J. O. Jilek et al., Collect.Czech.Chem.Commun. 33, 1831–1845, especially 1842 (1968)] are dissolved, with 6 g of tris-triphenylphosphine-rhodium chloride, in 1,200 ml of highest purity benzene and hydrogenated catalytically in an autoclave at 90°–100° C and an initial hydrogen pressure of 50 bars.

The hydrogenation is discontinued after 2 hours and the resulting black solution is evaporated in vacuo to give an oil. Hot hexane is added to the viscous oil and the mixture is filtered hot through a column containing 80 g of silica gel. The column is rinsed with 150 ml of warm hexane and the combined eluates are evaporated to dryness. The crystalline residue is recrystallised from 1,000 ml of pentane. The resulting 2-chloro-10,11-dihydro-dibenzo[b,f]-thiepine melts at 64°–65° C.

b. 49.2 g (0.2 mol) of 2-chloro-10,11-dihydro-dibenzo[b,f]thiepine are dissolved in 600 ml of absolute ethanol at the reflux temperature and 160 ml of 30 % strength aqueous hydrogen peroxide solution is added dropwise in the course of 30 minutes whilst stirring vigorously. The reaction mixture is boiled under reflux for 12 hours and is then poured into 1,200 ml of ice water. The precipitated reaction product is filtered off, washed well with cold water and recrystallised moist from ethanol. The resulting 2-chloro-10,11-dihydrodibenzo[b,f]thiepine-5-oxide melts at 116°–118° C.

EXAMPLE 7

Analogously to Example 5, starting from 20.8 g (0.080 mol) of 2-chloro-dibenzo[b,f]thiepine-5-oxide and 21.5 g (0.10 mol) of O-(mesitylenesulphonyl)-hydroxylamine, 2-chloro-5,5-dihydro-5-imino-dibenzo[b,f]thiepine-5-oxide of melting point 124°–125° C (from ethyl acetate/petroleum ether) is obtained.

The starting material is manufactured as follows:

a. 24.4 g (0.1 mol) of 2-chloro-dibenzo[b,f]thiepine are dissolved in 300 ml of absolute ethanol at the reflux temperature and 80 ml of 30 % strength aqueous hydrogen peroxide solution are added dropwise in the course of 30 minutes whilst stirring vigorously. The reaction mixture is boiled under reflux for 12 hours and is then poured into 600 ml of ice water. The precipitated reaction product is filtered off, washed well with cold water and recrystallised from ethanol. The resulting 2-chlorodibenzo[b,f]thiepine5-oxide melts at 153°–156° C.

EXAMPLE 8

2.28 g (0.010 mol) of 10,11-dihydro-dibenzo[b,f]-thiepine-5-oxide are dissolved in 60 ml of absolute chloroform and 2.95 g (0.030 mol) of sodium azide are added. 12.8 g (0.120 mol) of concentrated sulphuric acid are then slowly added dropwise, at 45° C, whilst stirring vigorously, in the course of one hour. The reaction mixture is stirred at 45° C for a further 6 hours, then cooled to room temperature and poured into 200 ml of ice water. The pH value of the resulting mixture is brought to 6 with concentrated sodium hydroxide solution and the mixture is extracted with twice 100ml of methylene chloride. The organic phases are washed with water until neutral and dried over magnesium sulphate. The solvents are evaporated in vacuo and the residue is chromatographed on 15 g of silica gel using methylene chloride as the solvent and eluant, 50 ml fractions being separated off. Fractions 4 to 10 are combined and evaporated and the residue is recrystallised from benzene/petroleum ether. The resulting 5,5,10,11-tetrahydro-5-imino-dibenzo[b,f]thiepine-5-oxide melts at 115°–118° C.

The starting material is manufactured as follows:

a. 21.2 g (0.1 mol) of 10,11-dihydro-dibenzo[b,f]-thiepine [compare J. O. Jilek et al., Monatsh.Chem. 96, 182–207, especially 207, (1965)] are dissolved in 300 ml of absolute ethanol at the reflux temperature and 80 ml of 30% strength aqueous hydrogen peroxide solution is added dropwise in the course of 30 minutes whilst stirring vigorously. The reaction mixture is boiled under reflux for 12 hours and is then poured into 600 ml of ice water. The precipitated reaction product is filtered off, washed well with cold water and recrystallised moist from ethanol. The resulting 10,-11-dihydro-dibenzo[b,f]thiepine-5-oxide melts at 120°–121° C.

EXAMPLE 9

12 ml of acetone are poured onto a mixture of 2.26 g (0.010 mol) of 5,5-dihydro-5-imino-dibenzo [b,f]thiepine and 1.47g (0.011 mol) of N-chlorosuccinimide and the solution is stirred for 6 minutes at room temperature. The reaction mixture is then poured into ice water and the resulting oily N-chloro compound is taken up in methylene chloride by extracting three times. The combined methylene chloride solutions are washed once with ice water and dried at 0° C over sodium sulphate and the solvent is then evaporated in vacuo at a bath temperature of at most 10° C. dissolved The crude 5-(N-chloroimino)-5,5-dihydro-dibenzo[b,f]-thiepine, which remains as an oil, is cooled with ice and a solution of 0.44 g (0.011 mol) of sodium hydroxide in 80 ml of methanol is poured on and the mixture is then stirred for 16 hours at 45° C. The clear reaction mixture is neutralised with dilute hydrochloric acid and the methanol is evaporated in vacuo. Water is added to the residue and the mixture is extracted three times with methylene chloride. The combined organic phases are washed with saturated sodium chloride solution, dried over sodium sulphate and evaporated in vacuo. The residue is dissolved in toluene/methanol (4:1) and the solution is chromatographed on a column of 200 g silica gel. Toluene/methanol (4:1) is used as the eluant. The fractions which contain the crude product are combined and evaporated. The residue is dissolved in benzene and recrystallised with addition of hexane. After drying, the resulting 5,5-dihydro-5-imino-dibenzo[b,f]thiepine-5-oxide melts at 160°–161° C.

EXAMPLE 10

1.14 g (0.026 mol) of a 55% strength dispersion of sodium hydride in paraffin oil are stirred, under a nitrogen atmosphere, with 10 ml of pentane. The liquid phase is then removed by decanting off and subsequently filtering.

Initially 100 ml of absolute dimethylformamide are added to the residue and 5.8 g (0.024 mol) of 5,5-dihydro-5-iminodibenzo[b,f]thiepine-5-oxide are then added whilst stirring, whereupon the evolution of hydrogen starts. The dispersion is stirred for 30 minutes at room temperature until no further evolution of hydrogen can be detected and 3.90 g (0.028 mol) of methyl iodide are then slowly added dropwise. The reaction mixture is stirred for 3 hours at room temperature and is then substantially concentrated in a waterjet vacuum. The residue is taken up in 200 ml of ether, 100 ml of pentane and 50 ml of methylene chloride and the mixture is extracted with twice 50 ml of water. The organic phase is dried over sodium sulphate and evaporated in a waterjet vacuum. 5,5-Dihydro-5-(methylimino)-dibenzo[b,f]thiepine-5-oxide remains as a residue and, after a single recrystallisation from methylene chloride/cyclohexane, melts at 139°–141° C.

EXAMPLE 11

1 g (0.004 mol) of 5,5-dihydro-5-imino-dibenzo[b,f]-thiepine-5-oxide is dissolved in 40 ml of absolute benzene and the solution is heated to 90°–100° C with 0.2 g of tristriphenylphosphine-rhodium chloride in a closed vessel in a hydrogen atmosphere under an initial pressure of 50–60 bars until the absorption of hydrogen has ceased. The reaction solution is evaporated to dryness in a water jet vacuum. The residue is dissolved in 20 ml of methylene chloride and ethereal hydrogen chloride solution is added until the solution is slightly acid to congo red. 5,5,10,11-Tetrahydro5-imino-dibenzo[b,f]-thiepine-5-oxide hydrochloride, which has precipitated, is filtered off and rinsed with ether, after which it melts at 230° C (with decomposition).

EXAMPLE 12

2.4 g (0.010 mol) of 5,5-dihydro-5-imino-dibenzo[b,f]-thiepine-5-oxide are dissolved in 20 ml of acetone and 1.15 g (0.010 mol) of maleic acid are added. 5,5-Dihydro-5-iminodibenzo[b,f]thiepine-5-oxide maleate which has precipitated, is filtered off and rinsed with ether. It melts at 126°–127° C.

EXAMPLE 13

Analogously to Example 1, 11.7 g (0.040 mol) of 2-methoxy-5,5-dihydro-5-imino-dibenzo[b,f]thiepine hydrochloride are oxidised with 9.5 g (0.044 mol) of sodium periodate in a mixture of 350 ml of methanol and 280 ml of water. After recrystallisation of the crude product from ethyl acetate/petroleum ether, 2-methoxy-5,5-dihydro-5-iminodibenzo[b,f]thiepine-5-oxide, of melting point 126128° C, is obtained.

2-Methoxy-5,5-dihydro-5-imino-dibenzo[b,f]thiepine, which is required as the starting material, can be manufactured as follows:

a. 14.4 g (0.060 mol) of 2-methoxy-dibenzo[b,f]thiepine of melting point 84°-91° C [compare K. Pelz et al., Coll. Czech.Chem.Comm. 33, 1889–1916 (1968)] are dissolved in 200 ml of methylene chloride and 15.5 g (0.072 mol) of 0-methylenesulphonyl-hydroxylamine are added at room temperature whilst stirring. The reaction mixture is stirred for 15 hours at room temperature and the sodium methoxide solution obtained from 1.65 g (0.072 mol) of sodium and 20 ml of methanol, is then added at −5° C. The mixture is stirred for one hour at 0° C and then washed three times with water. The organic phase is dried over magnesium sulphate and the solvent is evaporated in vacuo. The crude 2-methoxy-5,5-dihydro-5-imino-dibenzo[b,f]thiepine, which remains as an oil, is treated with ethanolic hydrochloric acid and the resulting hydrochloride is recrystallised from ethanol/ethyl acetate. The resulting 2-methoxy-5,5-dihydro-5-imino-dibenzo[b,f]thiepine hydrochloride melts at 235°-237° C.

EXAMPLE 14

Analogously to Example 2, 2-fluoro-5,5-dihydro-5-imino-dibenzo[b,f]thiepine-5-oxide is manufactured from 2.80 g (0.010 mol) of 2-fluoro-5,5-dihydro-5-imino-dibenzo [b,f]thiepine hydrochloride; 2-bromo-5,5-dihydro-5-iminodibenzo[b,f]thiepine-5-oxide is manufactured from 3.41 g (0.010 mol) of 2-bromo-5,5-dihydro-5-imino-dibenzo[b,f]thiepine hydrochloride; 2-(trifluoromethyl)-5,5-dihydro-5-imino-dibenzo[b,f]thiepine-5-oxide is manufactured from 3.30 g (0.010 mol) of 2-(trifluoromethyl)-5,5-dihydro-5-imino-dibenzo[b,f]thiepine hydrochloride; and 5,5-dihydro-5-imino-10,11-dimethyl-dibenzo[b,f]thiepine-5-oxide is manufactured from 2.89 g (0.010 mol) of 5,5-dihydro-5-imino-10,11-dimethyl-dibenzo[b,f]thiepine hydrochloride.

The starting materials are manufactured analogously to Example 2a) starting from 22.6 g (0.10 mol) of 2-fluorodibenzo[b,f]thiepine, 28.7 g (0.10 mol) of 2-bromo-dibenzo-[b,f]thiepine, 27.6 g (0.10 mol) of 2-(trifluoromethyl)-dibenzo[b,f]thiepine and 23.5 g (0.10 mol) of 10,11-dimethyldibenzo[b,f]thiepine respectively.

The two first mentioned compounds and their manufacture have been described by J. O. Jilek et al., Collect. Czech. Chem. Commun. 33, 1831–45 (1968). With regard to the compound mentioned third compare K. Pelz et al., Collect. Czech. Chem. Commun. 34, 3936–43 and with regard to the last mentioned compound compare M. M. Urberg and E. T. Kaiser, J. Am. Chem. Soc. 89, 5931 (1967).

EXAMPLE 15

1.42 g (0.005 mole) of 5,5-dihydro-5-(acetylimino)-dibenzo[b,f]thiepin-5-oxide is stirred in 100 ml of a 1% potassium hydroxide solution in ethanol/water 9:1 for 15 hours at room temperature. The resulting light-yellow solution is subsequently concentrated in a water-jet vacuum to about 10 ml and then extracted with 100 ml of chloroform. The chloroform solution is washed neutral with water, dried over sodium sulphate and concentrated by evaporation. There remains as residue 5,5-dihydro-5-imino-dibenzo[b,f]thiepin-5-oxide, m.p. 154°-156°.

The starting material can be produced for example as follows:

a. 2.4 g (0.010 mole) of 5,5-dihydro-5-imino-dibenzo[b,f]thiepin-5-oxide is dissolved in 100 ml of benzene and 10 ml of pyridine, and an addition is made dropwise, with stirring, of 1 ml (1.1 g; 0.014 mole) of acetyl chloride. The reaction mixture is subsequently refluxed for two hours and then concentrated in a water-jet vacuum. The residue remaining is taken up in 150 ml of methylene chloride, and this solution is extracted successively with, in each case, 50 ml of 2N sodium carbonate solution, 5N hydrochloric acid and water. After drying over sodium sulphate and removal of the solvent by evaporation there remains as residue 5,5-dihydro-5-(acetylimino) -dibenzo[b,f]thiepin-5-oxide, m.p. 215°-216°.

EXAMPLE 16

2.4 g (0.010 mole) of 5,5-dihydro-5-imino-dibenzo[b,f]thiepin-5-oxide is refluxed together with 6 ml of formic acid and 3 ml of a 38% aqueous formaldehyde solution for 4 hours with stirring. The reaction solution is subsequently concentrated in a water-jet vacuum. The 5,5-dihydro-5-(methylimino)-dibenzo[b,f]thiepin-5-oxide remaining as residue melts at 139°-140° after a single recrystallisation from methylene chloride-hexane.

What we claim is:

1. A heterocyclic S-imino-S-oxide of the formula I

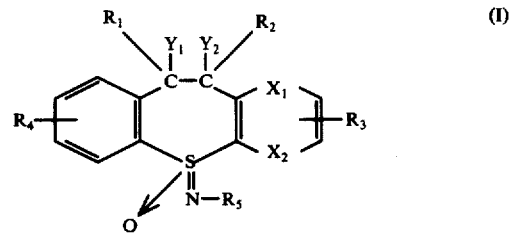

in which one of the symbols $X_1$ and $X_2$ denotes a direct bond and the other denotes the vinylene group —CH=CH— or the epithio radical —S—, $Y_1$ and $Y_2$ conjointly denote an additional bond or one of the symbols denotes hydrogen and the other denotes hydrogen or, conjointly with the symbol $R_1$ or $R_2$, which is present on the same carbon atom, denotes the oxo radical, one of the symbols $R_1$ and $R_2$ denotes hydrogen or lower alkyl and the other denotes hydrogen or lower alkyl or, conjointly with the symbol $Y_1$ or $Y_2$, which is present on the same carbon atom, denotes the oxo radical, or, if $Y_1$ and $Y_2$ conjointly denote an additional bond, also denotes lower alkoxy, and $R_3$ and $R_4$ independently of one another denote hydrogen, halogen up to atomic number 35, lower alkyl, lower alkoxy or trifluoromethyl and $R_5$ denotes hydrogen or lower alkyl, or a pharmaceutically acceptable acid addition salt thereof.

2. A compound according to claim 1 having the formula I given in claim 1, in which $Y_1$ and $Y_2$ denote hydrogen or conjointly denote an additional bond, $R_1$ and $R_2$ denote hydrogen or methyl, $R_3$ and $R_4$ independently of one another denote hydrogen, halogen up to atomic number 35, methyl, methoxy or trifluoromethyl and $R_5$ denotes hydrogen or methyl, whilst $X_1$ and $X_2$ have the meaning indicated in claim 1, or a pharmaceutically acceptable acid addition salt thereof.

3. A compound according to claim 1 having the formula I given in claim 1, in which $X_1$ denotes a direct bond and $X_2$ denotes the vinylene group or the epithio radical, $Y_1$ and $Y_2$ denote hydrogen or conjointly denote an additional bond, $R_1$, $R_2$ and $R_3$ denote hydrogen, $R_4$ denotes hydrogen, halogen up to atomic number 35 or methoxy, and $R_5$ denotes hydrogen or methyl, or a pharmaceutically acceptable acid addition salt thereof.

4. A compound according to claim 1 having the formula I given in claim 1, in which $X_1$ denotes a direct bond and $X_2$ denotes the vinylene group or the epithio radical, $Y_1$ and $Y_2$ denote hydrogen or conjointly denote an additional bond, $R_1$, $R_2$ and $R_3$ denote hydrogen, $R_4$ denotes hydrogen or, if $X_2$ is a vinylene radical can also denote chlorine or methoxy in the 2- or 8-position, and $R_5$ denotes hydrogen or methyl, or a pharmaceutically acceptable acid addition salt thereof.

5. A compound according to claim 1 which is 5,5-dihydro-5-imino-dibenzo[b,f]thiepine-5-oxide or its maleate salt.

6. A compound according to claim 1 which is 2-chloro-5,5-dihydro-5-imino-dibenzo[b,f]thiepine-5-oxide.

7. A compound according to claim 1 which is 5,5,10,11-tetrahydro-5-imino-dibenzo[b,f]thiepine-5-oxide or its hydrochloride salt.

8. A compound according to claim 1 which is 10,10-dihydro-10-imino-thieno[2,3-b] [1]benzo-thiepine-10-oxide.

9. A compound according to claim 1 which is 2-chloro-5,5,10,11-tetrahydro-5-imino-dibenzo[b,f]thiepine-5-oxide.

10. A compound according to claim 1 which is 5,5-dihydro-5-(methylimino)-dibenzo[b,f]thiepine-oxide.

11. An oral anticonvulsive preparation comprizing an anticonvulsively effective amount of a compound according to claim 1, wherein $X_1$, $X_2$, $Y_1$, $Y_2$, $R_1$, $R_2$, $R_3$, $R_4$ and $R_5$ have the meanings defined in claim 1, or a pharmaceutically acceptable acid addition salt thereof, together with a pharmaceutical carrier.

12. An oral anticonvulsive preparation according to claim 1, wherein an anticonvulsively effective amount of 5,5-dihydro-5-imino-dibenzo[b,f]thiepine-5-oxide or of a pharmaceutically acceptable acid addition salt thereof is present.

13. A method for inducing an anticonvulsant action in a warm-blooded animal in need of treatment comprising peroral administration to said animal of an anticonvulsively effective amount of a compound according to claim 1, wherein $X_1$, $X_2$, $Y_1$, $Y_2$, $R_1$, $R_2$, $R_3$, $R_4$ and $R_5$ have the meanings defined in claim 1, or of a pharmaceutically acceptable acid addition salt thereof.

14. A method according to claim 13 comprising peroral administration of an anticonvulsively effective amount of 5,5-dihydro-5-imino-dibenzo[b,f]thiepine-5-oxide or of a pharmaceutically acceptable acid addition salt thereof.

* * * * *